United States Patent [19]

Marcadis et al.

[11] Patent Number: 5,290,231
[45] Date of Patent: Mar. 1, 1994

[54] AUTO-INFLATING CATHETER CUFF

[75] Inventors: Stuart J. Marcadis, Portage, Ind.; James H. DeVries, Grand Rapids, Mich.

[73] Assignee: DLP, Inc., Grand Rapids, Mich.

[21] Appl. No.: 940,633

[22] Filed: Sep. 4, 1992

Related U.S. Application Data

[63] Continuation-in-part of Ser. No. 537,566, Jun. 13, 1990, Pat. No. 5,197,952.

[51] Int. Cl.$^5$ .............................................. A61M 29/00
[52] U.S. Cl. ........................................ 604/96; 604/98; 606/194; 128/673
[58] Field of Search ............................. 604/43, 93–95, 604/96–101, 264, 280; 606/191, 194; 128/207.15, 672, 673

[56] References Cited

U.S. PATENT DOCUMENTS

| | | | |
|---|---|---|---|
| 3,528,427 | 9/1970 | Sheridan | 604/268 |
| 3,583,404 | 6/1971 | McWhorter | 604/266 |
| 4,182,343 | 1/1980 | Inaba | 604/268 |
| 4,445,897 | 5/1984 | Ekbladh et al. | 604/43 |
| 4,508,533 | 4/1985 | Abramson | 604/45 |
| 4,850,969 | 7/1989 | Jackson | 604/96 |

OTHER PUBLICATIONS

Retrograde Coronary Capillary Perfusion . . . The Annals of Thoracic Surgery, vol. 21, No. 5, May 1976, p. 404.
Synchronized Retroperfusion of Coronary Veins . . . The American Journal of Cardiology, vol. 41, Jun. 1978, p. 1192.
Retrograde Coronary Sinus Perfusion . . . The Annals of Thoracis Surgery, vol. 34, No. 6, Dec. 1982, pp. 647–658.
Myocardial Protection by Retrograde Cardioplegia . . . Cardiac Surgery: State of the Art Reviews, vol. 2, No. 2, Feb. 1988, pp. 197/218.

Primary Examiner—C. Fred Rosenbaum
Assistant Examiner—Ronald K. Stright, Jr.
Attorney, Agent, or Firm—Barnes, Kisselle, Raisch, Choate, Whittemore & Hulbert

[57] ABSTRACT

A perfusion catheter for use in open heart surgery having an inflatable cuff adjacent the distal end in communication with the lumen of the catheter to self-inflate when perfusion liquid is introduced into the lumen. A plug in the lumen within the cuff causes lumen flow to by-pass from the proximal end of the cuff to the distal end of the cuff through transverse parts in the lumen. A flow restriction at the distal end of the lumen causes pressure build-up to inflate the cuff. A pressure monitoring lumen splices to the catheter tube to parallel the tube down to the distal end where it is in communication with the end of the catheter and also with the distal end of the cuff to register cuff pressure. An introducer shaft is provided to be inserted into the lumen to abut the plug to stiffen the catheter, thus facilitating insertion, and a stiffener spine at the cuff area of the catheter also provides rigidity to compensate for the weakening of the lumen resulting from the transverse ports. A cross-port between the pressure monitoring lumen and the main lumen distally of the cuff will register lumen pressure if both the main lumen and the monitoring lumen become occluded at the distal end of the catheter.

4 Claims, 2 Drawing Sheets

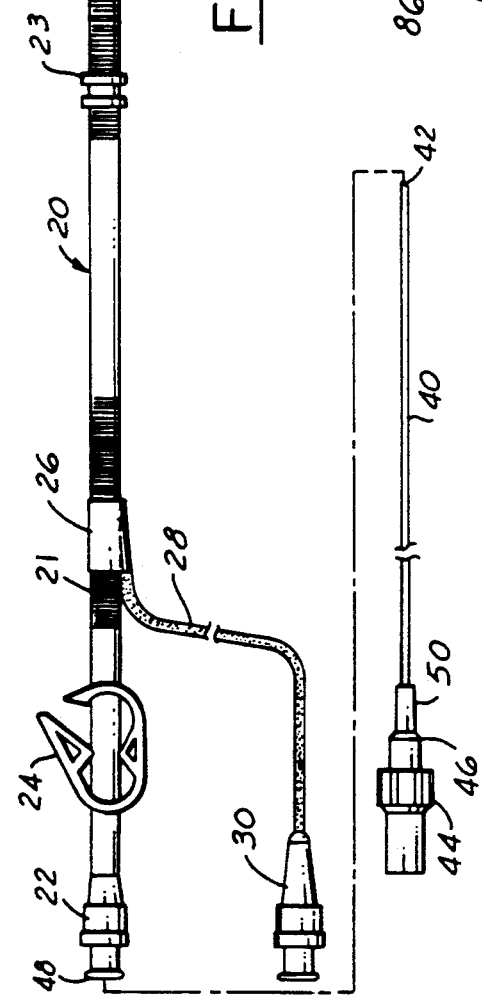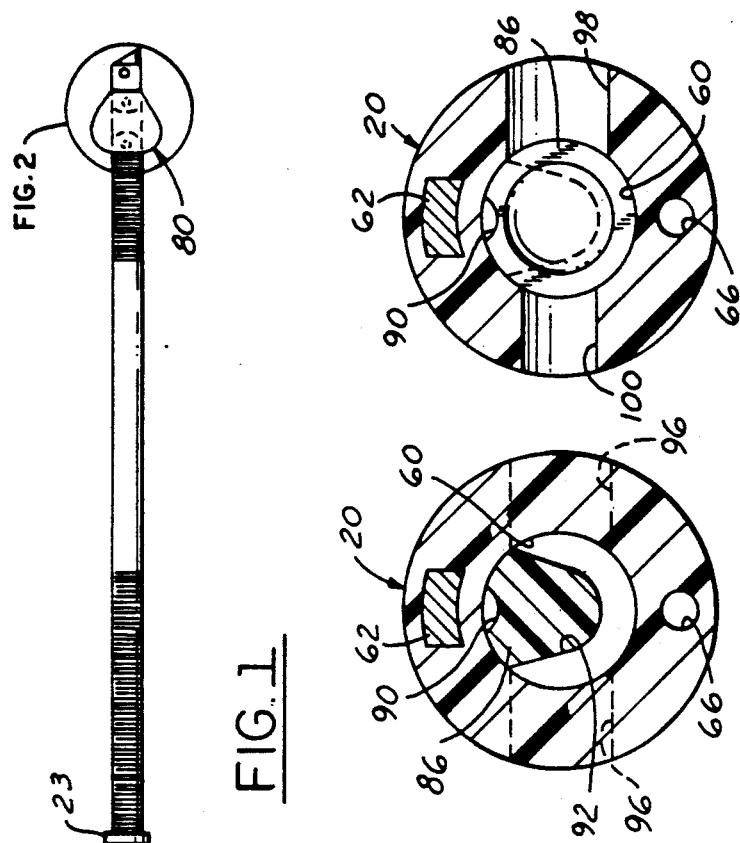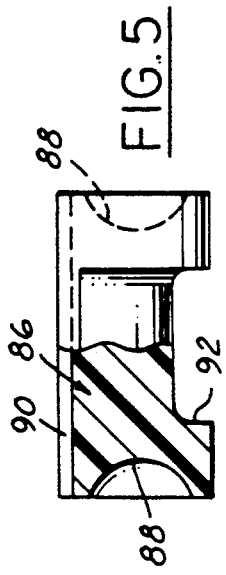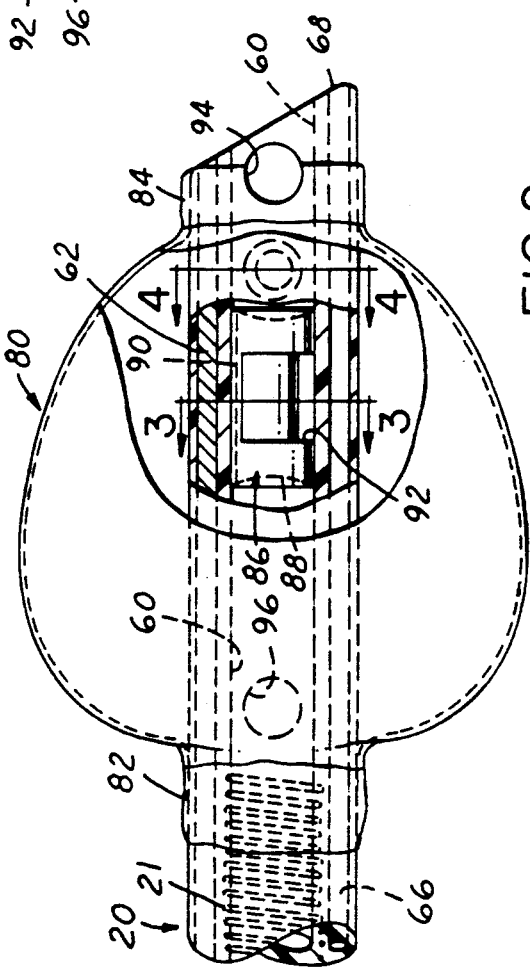

AUTO-INFLATING CATHETER CUFF

REFERENCE TO RELATED APPLICATIONS

This application is a continuation-in-part of Ser. No. 07/537,566 filed on Jun. 13, 1990 now U.S. Pat. No. 5,197,952.

Reference is made to a copending application filed concurrently herewith, Ser. No. 07/940,632 filed on Sep. 04, 1992.

FIELD OF THE INVENTION

Cardioplegic catheter for use in open heart surgery and with self-inflating retention cuff.

BACKGROUND AND OBJECTS OF THE INVENTION

In use of catheters for introduction into a body cavity, a process called catheterization, it is common in some instances to include on the catheter itself an inflatable balloon or "cuff" which is inflated after introduction of the catheter to prevent accidental retraction or rejection of the catheter. It is usual to inflate the cuff from an outside source of air as, for example, a bulb pump. Representative of the prior art in this field is a U.S. Pat. No. to Weikl et al, 4,573,966.

The present invention is directed to a self-inflating cuff which can be used when the catheter is utilized for perfusion of liquid into a body cavity. One known means of accomplishing this inflation is to provide the catheter with an inflatable cuff surrounding the outside of the catheter spaced from the distal end. Openings into the cuff from the catheter lumen are provided spaced axially of the lumen, and the sides of the distal end of the catheter are provided with a plurality of small openings for outflow of the perfusion liquid. The end of the lumen, in this known device, is closed off and the openings are designed such that the pressure in the lumen will exceed the pressure in the vessel and will, as a result, exert pressure on the interior of the cuff to cause inflation. Thus, pressure flow divides with a portion entering the cuff and a second larger portion exiting the catheter lumen. The fluid portion entering the cuff remains in the cuff as long as fluid is flowing through the lumen and therefore becomes stagnant. This is an undesirable condition particularly when blood or blood elements comprise part of the solution delivered through the catheter. See U.S. Pat. No. 5,021,045 (Jun. 04, 1991).

The cannulae may be placed in small friable vessels in the body. One known instance would be placement in the coronary sinus of the heart. Existing catheters monitor the pressure of the coronary sinus either at the end of the catheter or along the outside of the distal portion of the catheter. When the vessel size is close to the diameter of the catheter, the force of the pressure exiting the catheter through radially oriented holes can force the catheter against the wall of the vessel and thus cause the pressure monitoring port to become occluded. Similarly, a sharp turn in the vessel can cause the monitoring port at the tip or side to occlude. When the monitoring port is thus occluded, excessive pressure can be generated in the central lumen of the catheter and subsequently in the balloon, since flow through the cannulae is stopped or reduced. This excess pressure has been known to rupture the coronary sinus.

Similarly, catheters with multiple holes in the cuff area have a tendency to buckle in this area. A common means of preventing bucking in the catheter body is to include a reinforcing wire spring into the wall of the catheter. However, it is difficult to continue this spring into the cuff area since punching the holes will expose many sharp ends that could damage the cuff.

The present invention provides an improved self-inflating cuff which reduces stagnation of inflating media in the cuff. All of the fluid passing through the catheter exits the lumen at the cuff, passes through the chamber formed between the cuff and the outside of the catheter, and returns to the catheter lumen for subsequent delivery to the body cavity. A further object is to provide a reinforcement to prevent unintentional collapse of the catheter in the cuff area. Pressure monitoring is important in the use of a perfusion function and an object is also to allow monitoring of the cuff pressure and central lumen pressure as well as the approximation of vessel pressure depending upon the flow through the catheter.

Pressure that approximates the intra-vessel condition in normal operation will be sensed through the pressure lumen and its associated openings. However, should the lumen of the catheter become blocked simultaneously with the outlet of the pressure monitoring lumen, the opening between the pressure lumen and the catheter lumen will indicate undue pressure in the cuff which requires immediate attention of the monitoring personnel. Other objects include a lumen plug which serves the dual purpose of assisting in the introducing of the distal end of the catheter into a vessel, and diverting flow from the lumen through the balloon and subsequently into the distal portion of the lumen beyond the plug.

Other features of the invention will be apparent in the following description and claims in which the invention is described together with details to enable persons skilled in the art to practice the invention, all in connection with the best mode presently contemplated for the invention.

BRIEF DESCRIPTION OF THE DRAWINGS

DRAWINGS accompany the disclosure, and the various views thereof may be briefly described as:

FIG. 1, an elevation of a perfusion catheter with a pressure monitor tube and an introducer stylet.

FIG. 2, an enlarged portion partially in section of the cuff area of FIG. 1 enclosed in the circle.

FIG. 3, a sectional view on line 3—3 of FIG. 2.

FIG. 4, a sectional view on line 4—4 of FIG. 2.

FIG. 5, a sectional view of a plug used in the lumen of the catheter.

BRIEF DESCRIPTION OF THE INVENTION

Figure 6:
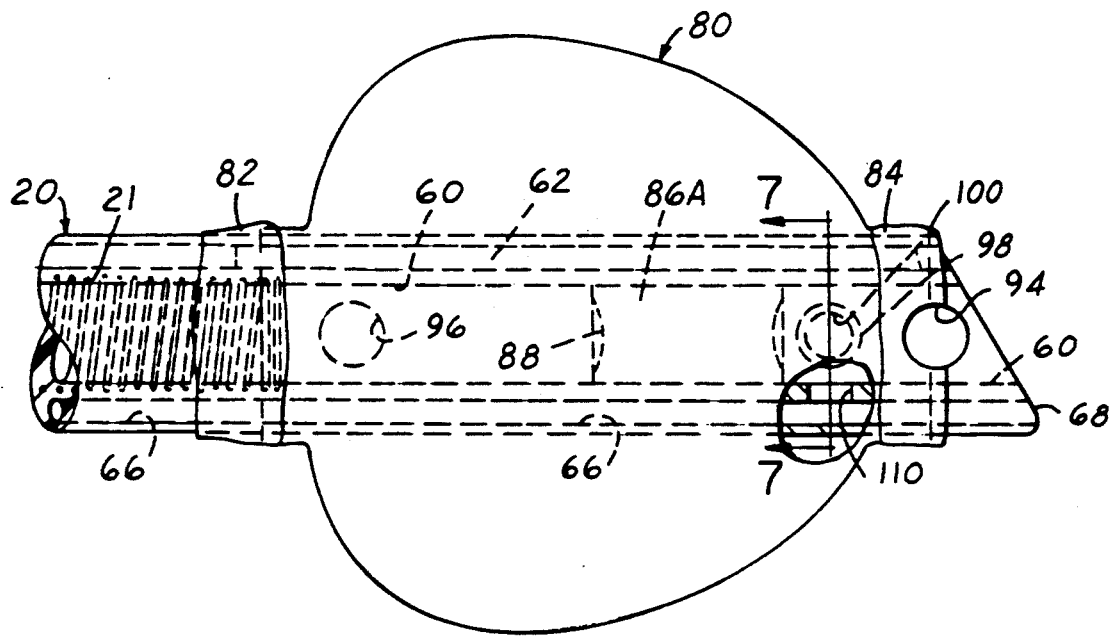
FIG. 6, a modification illustrating a pressure monitor port in the lumen for the cuff pressure.

A perfusion catheter having a distal end for introduction into the cavity of a body organ, as, for example, introducing cardioplegic liquid into a heart organ, which has a lumen blocked at an area of the distal end by a plug, the area being surrounded by an inflatable cuff. The interior of the cuff is in communication with the lumen to allow flow of liquid into and out of the cuff with a sufficient restriction at the distal end of the lumen to create an inflating pressure in the cuff when perfusion liquid is directed through the catheter. A reinforcing spine overlies the cuff area to resist kinking. An introducer shaft projectible into the catheter abuts a recess in the plug to allow pressure to be applied to the distal end during the introducing phase. A cross-port connects the main lumen with the pressure monitoring lumen distal of the cuff to register pressure in the main lumen in the event of occlusion.

DETAILED DESCRIPTION OF THE INVENTION AND THE MANNER OF AND PROCESS OF USING IT

The catheter to be described is frequently used in the introduction of cardioplegic fluid (cooling fluid) into a heart at the beginning of and during an open heart surgical operation. In this procedure, it is important not only that the catheter remain in place but that a means be provided to prevent the cardioplegic solution from leaking around the catheter. Thus the use of the inflatable retention cuff is indicated to provide a seal within the heart. It is also important that a surgeon or a perfusionist be able to monitor the pressure in the heart cavity receiving the cardioplegic liquid. Monitoring pressure in the inflatable cuff and the lumen of the catheter is also important in instances where internal pressures may increase significantly due to the tip of the catheter being inadvertently occluded during manipulation of the heart while delivering in the cardioplegic solution.

With reference to the drawings, in FIG. 1 an elevation of the catheter assembly is illustrated. The catheter body 20 is formed of a flexible plastic material with a reinforcing coiled spring 21 embedded in the wall of the plastic. A connector hub 22 at the proximal end is used to connect the catheter to a source of liquid in the use of the catheter for infusion. A slip ring 23 serves to aid in the manipulation of the catheter and provides an additional aid in maintaining the catheter in place. A close-off snap-lock 24 is provided for use in a closing of the catheter. A band 26 surrounds a pressure monitoring tube 28 at the point where the tube 28 splices into the catheter body 20 and extends parallel to a lumen 60 in the body and down to the distal end of the catheter body.

Also, in FIG. 1, an introducer shaft 40 has a blunt distal end 42 and a hub 44 with a first cylindrical section 46 to abut the end 48 of hub 22 and a second tapered section 50. This section 50 is dimensioned to move into the end 48 of hub 22 in a slip-lock relationship useful in the introduction of the catheter into a body organ as will be later described.

Looking now at FIG. 2, an enlarged area of the distal end of the catheter is shown, partially in section. The catheter has a lumen 60 extending from the proximal to the distal end. The section distal to the plug 86 may be reduced (both internal and external diameters) or increased lengthwise to create a pressure drop as fluid exits the catheter. A spine element 62 rigid to semi-rigid is inserted off-center into the wall of the catheter tube at the distal end as shown in sectional views FIGS. 3 and 4. The spine element 62 is extended from close to the distal end of the catheter back into the area proximal to the cuff to prevent the portion of the catheter distal to the proximal end of the cuff from kinking on insertion. This kinking can occur where perforations in the catheter tube are located.

The pressure monitoring tube 28 joins with an incorporated passage 66 in the catheter tube wall, this passage being open at 68 to the distal end of the catheter and at 110 (FIGS. 6 and 7) to the lumen of the catheter as explained in greater detail below.

Turning now to the inflatable retention cuff 80 shown in FIGS. 1 and 2, the cuff, formed of relatively thin flexible membrane that will retain the inflationary fluid during use, is enlarged at one end and tapered down to the distal end. This cuff compresses, and may deflate entirely, when the distal end of the catheter is introduced to the body organ.

Figure 7:
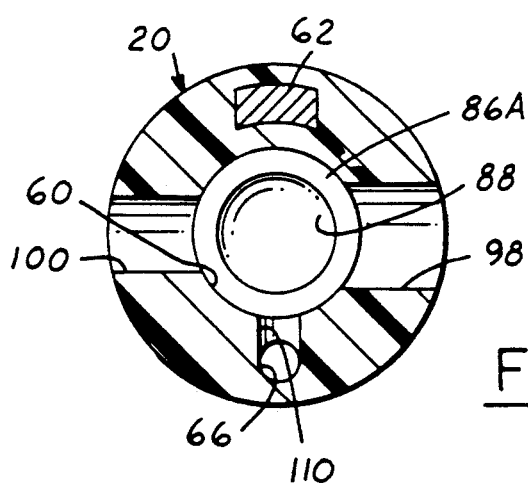
FIG. 7, a section on line 7—7 of FIG. 6.

The cuff 80 has two sleeve ends 82,84 which are snugged and sealed around the tube 20 at each end of the cuff. In the lumen 60 between the ends of the cuff 80 is inserted and fixed a lumen plug 86 which is cylindrical in basic shape and symmetrical. Each end preferably has a locator recess 88 as shown in FIG. 5 for receiving the blunt end of an introducer shaft as will be described. The plug is preferably placed toward the distal end of the area enclosed by the cuff 80. In the embodiment of FIGS. 1 to 5, a shallow axial restricted passage 90 on the surface of the plug 86 is open to the lumen 60 at each end. While each end of the plug 86 is cylindrical in shape with a relatively tight fit with the interior walls of the lumen, the central part of the plug is provided with a partial girdling recess 92 as shown best in FIG. 3. The purpose of this recess 92 relates to the installation of the plug 86 near the distal end of the lumen. The recess makes it easier to introduce the plug into the lumen. Once the plug is properly positioned, a silicon adhesive (RTV) may be introduced into the cavity 92 through a blunt needle on a syringe to fill the cavity and lock the plug 86 securely in place. The plug then becomes essentially a solid cylinder of material as shown in FIGS. 6 and 7. Alternately, viscous silicone adhesive can be injected in the lumen to form a solid cylinder if the axial passage is not required.

The lumen 60, as described above, opens to the distal end of the catheter. Side opening ports 94 are provided to allow perfusion fluid to escape in the event the end of the lumen is closed by inadvertent contact with a body part. The length of the catheter distal to the balloon may be increased substantially in length if desired in other configurations. The lumen, however, also is open to the interior of the cuff 80 by side ports 96 at the proximal end of the cuff and at the distal end through opposed ports 98 and 100 shown in FIG. 2. The ports 96,98 and 100 are proportioned in diameter to provide the described inflation pressure in the cuff during the use of the catheter. When the total effective area of side ports 96 is larger than the area of ports 98,100 (FIGS. 3 and 4), the restricting pressure of the exit ports 98,100 will cause pressure in ports 96 to inflate the cuff. The flow from the lumen 60 through the cuff is first through the ports 96 to the interior of the cuff and then out of the cuff through port 98 and ensmalled port 100 back to the lumen. If the section of catheter containing lumen has been reduced in size as discussed above, the precise size of these ports is not critical.

In FIGS. 6 and 7, a modification is illustrated in which the same reference characters are applied as in FIG. 2 for the same parts. The broken circle in FIG. 6 and the sectional view on line 7—7 of FIG. 6 show a short radial passage 110 extending from the pressure monitoring passage 66 to the lumen 60 within the area covered by the cuff 80. Thus, the pressure being monitored in passages 28 and 66 will approximate the pressure at the distal end (intra-vessel pressure) in normal operation and intra-cuff or lumen pressure should the tip be occluded and flow through the cannula thereof stopped. In this embodiment in FIGS. 6 and 7, the passage 90 (FIGS. 3 and 4) is eliminated, thus presenting a solid plug 86A.

Figure 8:
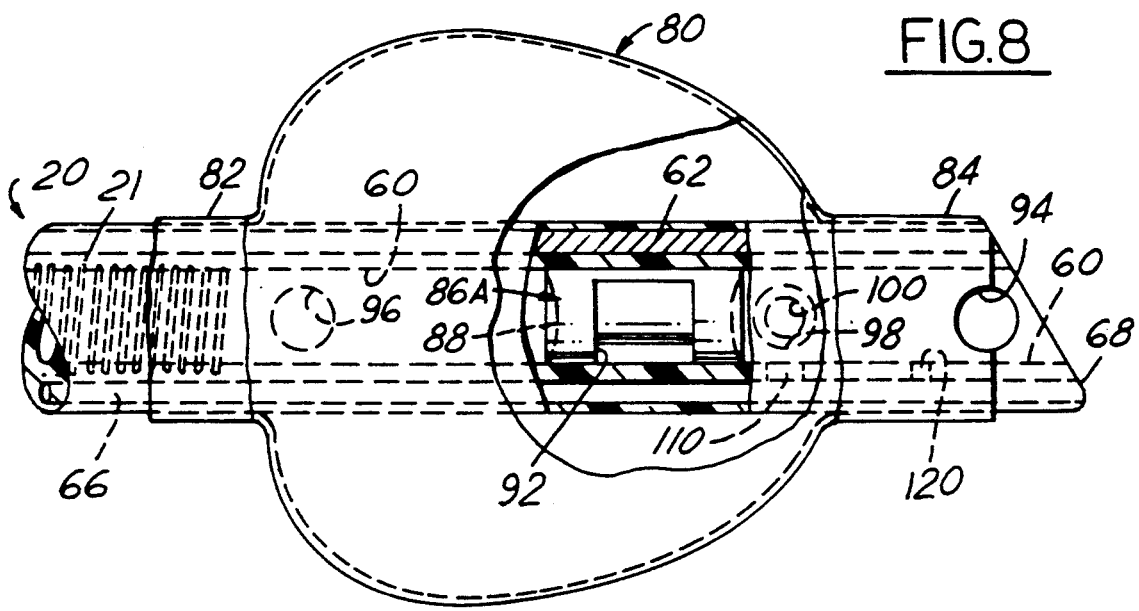
FIG. 8, a longitudinal section illustrating a modified catheter with a cross-port from monitor lumen to main lumen.

A modification is illustrated in FIG. 8 in which the structure is the same as shown in FIG. 6 with the exception that the catheter is extended somewhat beyond the cuff 80 and a cross-port 120 is provided connecting the pressure monitor lumen 66 and the main lumen 60. As described, passage 110 connects the distal end of the cuff with the monitor lumen 66. In the modification, should the main lumen 60, the ports 94, and the monitor lumen 66 become occluded, the cross-port would register the pressure in the main lumen distal of the cuff.

In the operation of the described catheter, the first step in the use is the introduction of the catheter into a heart chamber. This is preferably accomplished by the use of an introducer shaft 40 having the hub elements 44,46 and 50. This shaft 40 is projected into the lumen 60 of the catheter and moved down so that the blunt end 42 contacts the hollowed recess 88 of the plug 86. Pressure is then applied to the hub element 44 to stretch out the catheter tube and the tapered element 50 is introduced into the catheter stylet 48 in what is referred to as a slip-lock connection. This tensioning of the catheter stiffens it for the introduction phase.

Once the distal end of the catheter is moved through the wall of the body element together with the deflated cuff, the introducer shaft may be released from the hub 22,48 and withdrawn. The catheter is now ready for connection to a perfusion system. The hub 30 of the pressure monitor line may then be connected to a fluid filled pressure monitor system as is well known. The closed nature of normal monitoring systems prevent fluid flowing from lumen 60 into lumen 66 and subsequently out of the catheter. A stopcock (not shown) is typically connected to the hub 30 to serve as a closing means during insertion.

The recess 88 is provided better to translate the axial force created by the introducer shaft in stretching (tensioning as above) toward the distal tip. The distance between the side ports 96 and the plug 86 is provided so that the introducer end 42 will not escape from the lumen into the walls of the cuff should the end of the catheter buckle unexpectedly during the introduction procedure.

What is claimed is as follows:

1. A perfusion catheter which is to be used for introduction into a body cavity comprising:
    (a) a proximal end for introduction of fluid,
    (b) a distal end for introduction into a body cavity,
    (c) a connecting tube between said proximal and distal ends comprised of a flexible material having a central lumen connecting said ends,
    (d) an inflatable cuff enclosing part of said tube adjacent the distal end of the catheter and sealed at each end on said tube,
    (e) a lumen plug in said central lumen positioned within that part of said tube enclosed by said cuff,
    (f) one or more openings in said lumen within said cuff to admit lumen fluid into said cuff, and means restricting the flow of lumen fluid distally of said plug to create an inflating pressure in said cuff,
    said central lumen having a first opening at the distal end of said central lumen in the tip end of said catheter,
    (g) a pressure monitoring lumen associated with said connecting tube open to the distal end of said tube, and
    (h) a second opening in the form of a cross-port between said central lumen and said monitoring lumen distal of said cuff and proximal to the end of said tube to monitor pressure in said central lumen in the event of occlusion of the first opening at the distal end of said central lumen.

2. The perfusion catheter set forth in claim 1 wherein said pressure monitoring lumen is enclosed with a wall of said connecting tube.

3. A perfusion catheter for introduction into a body cavity comprising:
    a proximal end for introduction of fluid,
    a distal end for introduction into a body cavity,
    a connecting tube between said proximal and distal ends comprised of a flexible material having a central lumen connecting said ends,
    an inflatable cuff enclosing part of said tube adjacent to the distal end of the catheter and sealed at each end on said tube,
    means including one or more openings in said lumen within said cuff to admit lumen fluid into said cuff, and means restricting flow of lumen fluid to create an inflating pressure in said cuff,
    said central lumen having a first opening at the distal end of said central lumen in the tip end of said catheter,
    a pressure monitoring lumen associated with said connecting tube open to the distal end of said tube, and
    a second opening in the form of a cross-port between said central lumen and said monitoring lumen distal of said cuff and proximal to the end of said tube to monitor pressure in said central lumen in the event of occlusion of the first opening at the distal end of said central lumen.

4. The perfusion catheter set forth in claim 3 wherein said pressure monitoring lumen is enclosed within a wall of said connecting tube.

* * * * *